US006992062B2

(12) United States Patent
Usala

(10) Patent No.: US 6,992,062 B2
(45) Date of Patent: Jan. 31, 2006

(54) METHOD OF STIMULATION HAIR GROWTH

(75) Inventor: Anton-Lewis Usala, Winterville, NC (US)

(73) Assignee: Encelle, Inc., Greenville, NC (US)

( * ) Notice: Subject to any disclaimer, the term of this patent is extended or adjusted under 35 U.S.C. 154(b) by 550 days.

(21) Appl. No.: 09/870,424

(22) Filed: May 30, 2001

(65) Prior Publication Data
US 2002/0065222 A1 May 30, 2002

Related U.S. Application Data

(60) Provisional application No. 60/208,116, filed on May 31, 2000.

(51) Int. Cl.
*A61K 38/00* (2006.01)
(52) U.S. Cl. .................................................. 514/12
(58) Field of Classification Search ................. 514/12, 514/21, 2
See application file for complete search history.

(56) References Cited

U.S. PATENT DOCUMENTS

| | | | |
|---|---|---|---|
| 4,198,479 A | 4/1980 | Tytell et al. | |
| 4,520,821 A | 6/1985 | Schmidt et al. | |
| 4,657,866 A | 4/1987 | Kumar | |
| 4,696,286 A | 9/1987 | Cochrum | |
| 4,797,213 A | 1/1989 | Parisius et al. | |
| 4,902,295 A | 2/1990 | Walthall et al. | |
| 4,950,483 A | 8/1990 | Ksander et al. | |
| 4,957,902 A | 9/1990 | Grinnell | |
| 5,021,349 A | 6/1991 | Drouet et al. | |
| 5,079,160 A | 1/1992 | Lacy et al. | |
| 5,128,360 A | 7/1992 | Cerami et al. | |
| 5,246,971 A | 9/1993 | Williamson et al. | |
| 5,263,983 A | 11/1993 | Yoshizato et al. | |
| 5,322,790 A | 6/1994 | Scharp et al. | |
| 5,358,969 A | 10/1994 | Williamson et al. | |
| 5,457,093 A | 10/1995 | Cini et al. | |
| 5,591,709 A | 1/1997 | Lindenbaum | |
| 5,605,938 A | 2/1997 | Roufa et al. | |
| 5,645,591 A | 7/1997 | Kuberasampath et al. | |
| 5,716,404 A | 2/1998 | Vacanti et al. | |
| 5,824,331 A | 10/1998 | Usala | |
| 5,830,492 A | 11/1998 | Usala | |
| 5,834,005 A | 11/1998 | Usala | |
| 5,840,059 A | 11/1998 | March et al. | |
| 5,852,009 A | 12/1998 | Cerami et al. | |
| 5,855,617 A | 1/1999 | Orton | |
| 6,046,160 A * | 4/2000 | Obi-Tabot ............... | 514/2 |
| 6,132,759 A | 10/2000 | Schacht et al. | |
| 6,197,330 B1 | 3/2001 | Rees et al. | |
| 6,231,881 B1 | 5/2001 | Usala et al. | |
| 6,238,888 B1 * | 5/2001 | Gentz et al. ............... | 435/69.4 |
| 6,261,587 B1 | 7/2001 | Usala | |
| 6,299,898 B2 | 10/2001 | Rees et al. | |
| 6,372,494 B1 * | 4/2002 | Naughton et al. ........... | 435/391 |
| 6,491,953 B1 * | 12/2002 | Sojka et al. ................ | 424/490 |
| 2002/0146439 A1 * | 10/2002 | DeLong et al. ............. | 424/401 |

FOREIGN PATENT DOCUMENTS

| | | |
|---|---|---|
| DE | 44 31 598 A1 | 3/1996 |
| EP | 0 213 908 A2 | 3/1987 |
| EP | 0 526 756 A | 2/1993 |
| EP | 0 564 786 A | 10/1993 |
| EP | 0 363 125 A2 | 10/1998 |
| WO | WO 91/09119 A1 | 6/1991 |
| WO | WO 92/19195 | 11/1992 |
| WO | WO 93/16685 | 9/1993 |
| WO | WO 93/16717 A1 | 9/1993 |
| WO | WO 93/24112 A1 | 12/1993 |
| WO | WO 94/03154 A1 | 2/1994 |
| WO | WO 94 08702 | 4/1994 |
| WO | WO 94/15589 A1 | 7/1994 |
| WO | WO 95/14037 | 5/1995 |
| WO | WO 95/19430 A1 | 7/1995 |
| WO | WO 97 20569 A | 6/1997 |
| WO | WO 97 39107 | 10/1997 |
| WO | WO 98/55161 A1 | 12/1998 |
| WO | WO 00/02596 A1 | 1/2000 |
| WO | WO 00/02999 A2 | 1/2000 |

OTHER PUBLICATIONS

U.S. Appl. No. 09/766,330, filed Jan. 19, 2001, Usala.
Hubbell et al., "Tissue Engineering," *Chemical & Engineering News*, (Mar. 13, 1995), pp. 42-54.
Isner et al., "Therapeutic Angiogenesis," *Frontiers in Bioscience*, vol. 3 (May 5, 1998) pp. 49-69.
Pennisi et al., "Mice Null for *Sox18* Are Viable and Display a Mild Coat Defect", *Molecular and Cellular Biology*, Dec. 2000, pp. 9331-9336, vol. 20, No. 24.
Ramsey et al., "Incidence, Outcomes, and Cost of Foot Ulcers in Patients with Diabetes", *Diabetes Care*, Mar. 1999, pp. 382-387, vol. 22, No. 3.
Ravin et al., "Long- and Short-Term Effects of Biological Hydrogels on Capsule Microvascular Density around Implants in Rats", *Neovascularization in Capsules*, Apr. 12, 2001, pp. 313-318.

* cited by examiner

Primary Examiner—Christopher R. Tate
Assistant Examiner—Maury Audet
(74) *Attorney, Agent, or Firm*—Alston & Bird LLP

(57) ABSTRACT

The invention provides a method of stimulating hair growth, comprising administering a therapeutic amount of a hydrogel matrix to an intradermal or subdermal site where hair growth is desired, the matrix composition comprising gelatin, such as denatured collagen, and a long chain carbohydrate, such as dextran. The matrix may further include polar amino acids, nitric oxide inhibitors and super oxide inhibitors. Injection is a preferred method of administration.

43 Claims, 4 Drawing Sheets

METHOD OF STIMULATION HAIR GROWTH

CROSS REFERENCE TO RELATED APPLICATIONS

This application claims the benefit of U.S. application Ser. No. 60/208,116, filed on May 31, 2000, which is incorporated by reference herein in its entirety.

FIELD OF INVENTION

The invention relates to methods of stimulating hair growth.

BACKGROUND OF THE INVENTION

Men, women, and children experience alopecia, the clinical term for hair loss. Androgenetic alopecia or pattern baldness, which is believed to result from a combination of genetic and hormonal causes, is by far the most common form of hair loss. It is the largest single type of recognizable alopecia to affect both men and women. The rate of hair shedding in androgenetic alopecia is affected by three forces: advancing age, an inherited tendency to bald early, and an over-abundance of the male hormone dihydrotestosterone (DHT) within the hair follicle. DHT is a highly active form of testosterone, which influences many aspects of behavior, from sex drive to aggression. The conversion from testosterone to DHT is driven by an enzyme called 5-alpha reductase, which is produced in the prostate, various adrenal glands, and the scalp. Over time, the action of DHT causes the hair follicle to degrade and shortens the anagen phase. Some follicles will gradually die, but most will simply shrink in size and produce weaker hairs. With a steadily shorter anagen growing cycle, more hairs are shed because the hairs becoming thinner and thinner until they are too fine to survive daily wear and tear. Balding hair gradually changes from long, thick, coarse, pigmented hair into fine, unpigmented vellus sprouts.

There is much debate on the mechanism that causes the hormonal degradation of the hair follicle, but it has been hypothesized that the hormone triggers an autoimmune response that initiates an attack on the hair follicle, resulting in destructive inflammation. It may be that androgens somehow alter the follicle, causing it to be labeled as a foreign body. The follicles then gradually wither under the onslaught of the attack. Another possible complementary explanation is that androgens also trigger increased sebum production, which favors an excessive microbial population that leads to the same inflammatory autoimmune response. In any case, hair progressively miniaturizes under the autoimmune attack, so that with each growth cycle it gets shorter and thinner until it finally turns into tiny unpigmented vellus hair.

Pattern hair loss appears to have other causes as well. For instance, damage to blood vessel linings can inhibit a growth factor they ordinarily produce: endothelium-derived relaxing factor (EDRF). MINOXIDIL™, a popular hair loss treatment, is thought to work, at least in part, by mimicking this growth factor. Similarly it has been noted that severe baldness is strongly correlated with heart disease and even diabetes, so there appears to be some common etiology outside of the strictly androgen paradigm for pattern loss. There are likely other factors as well.

Another type of hair loss, alopecia areata, affects millions to some degree, though it is usually temporary. Alopecia areata is a non-scarring, inflammatory, hair loss disease. The factors that activate the onset of alopecia areata and the mechanisms of its development are not fully understood. Circumstantial evidence suggests alopecia areata is an autoimmune disease where cells of an individual's own immune system prevent hair follicles from producing hair fiber.

There are other types of hair loss as well. For example, localized hair loss can result from the build-up of scar tissue around surgical or trauma-induced wound sites. There remains a need in the art for an effective hair growth stimulant in the art for treating hair loss.

SUMMARY OF THE INVENTION

It has been discovered that the matrix described herein is capable of successfully stimulating hair growth. The present invention involves the administration of a therapeutic amount of a hydrogel matrix to an area where hair growth is desired. Preferably, the matrix is applied by intradermal or subdermal injection.

The matrix of the invention preferably comprises a gelatin component, such as denatured collagen, at a concentration of about 0.01 to about 40 mM. The matrix also includes a long chain carbohydrate, such as dextran. The preferably concentration of dextran is about 0.01 to about 10 mM. Preferred embodiments of the matrix further include an effective amount of polar amino acids, one or more nitric oxide inhibitors, such as L-cysteine or L-arginine analogues, and a superoxide inhibitor, such as EDTA or salts thereof.

BRIEF DESCRIPTION OF THE DRAWINGS

Figure 1:
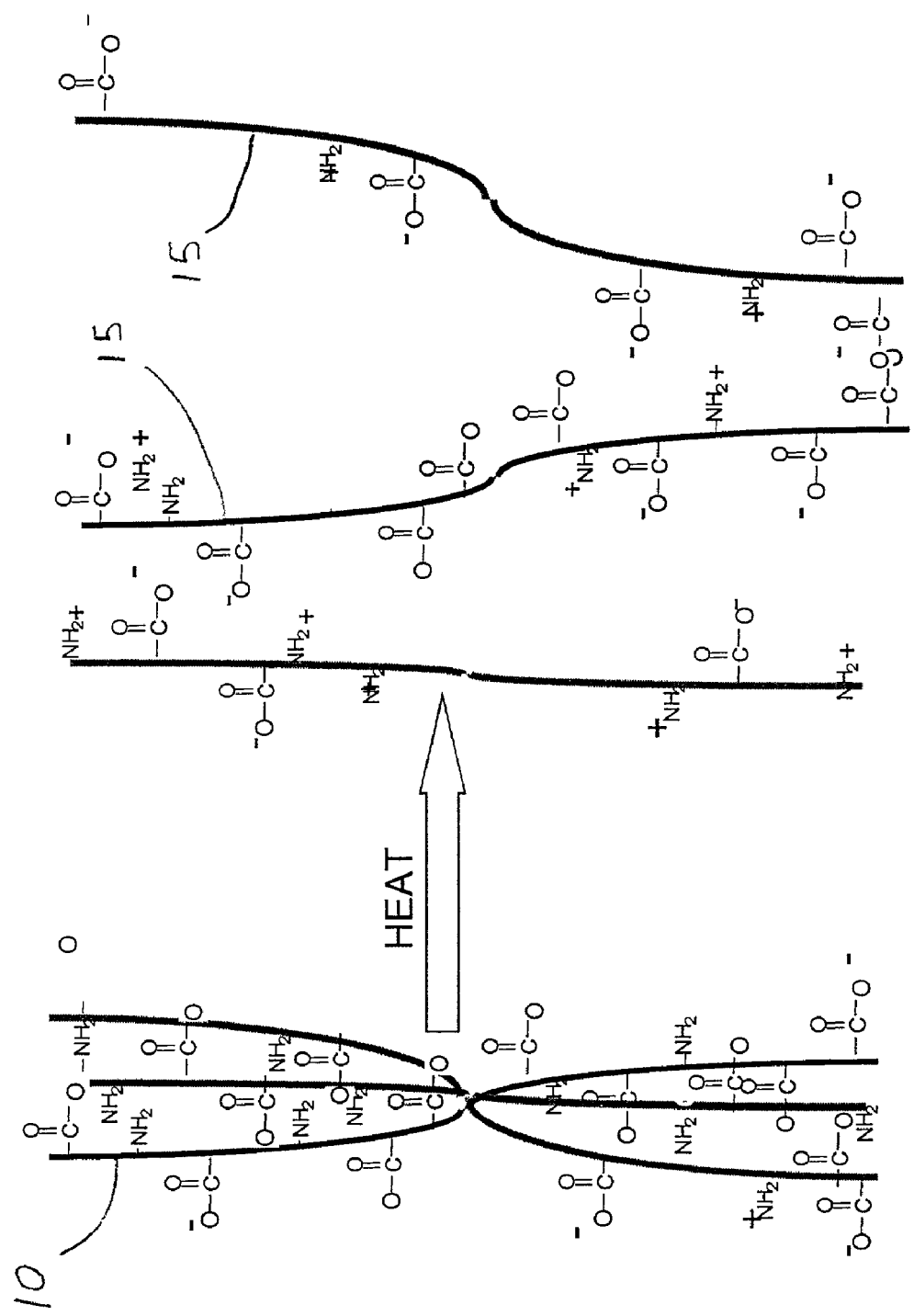
Figure 2A:
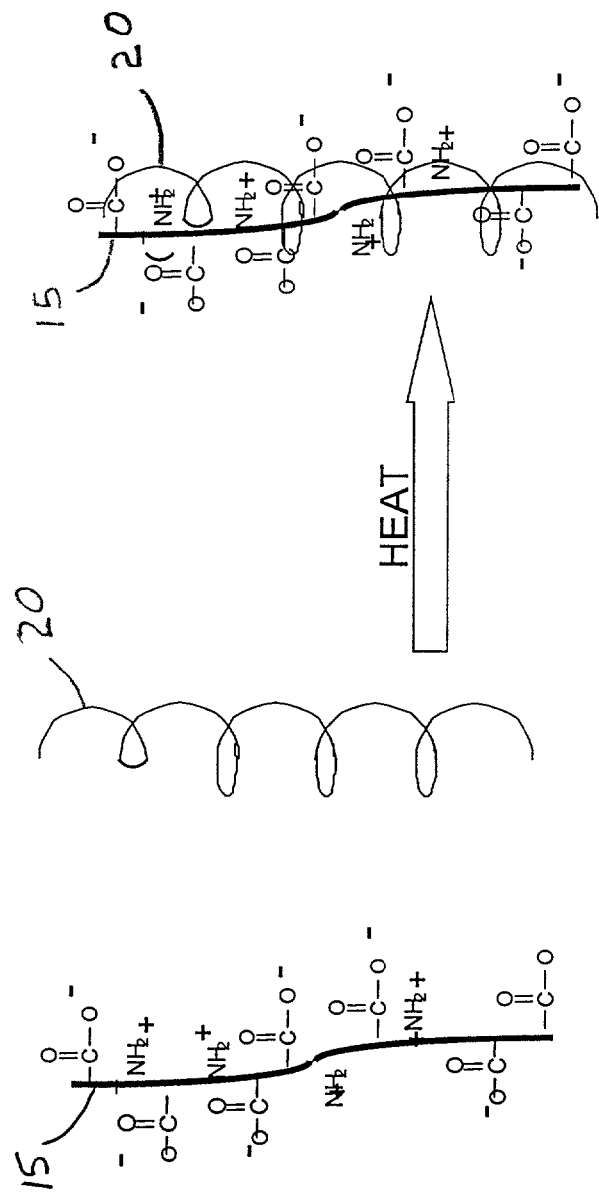
Figure 2B:
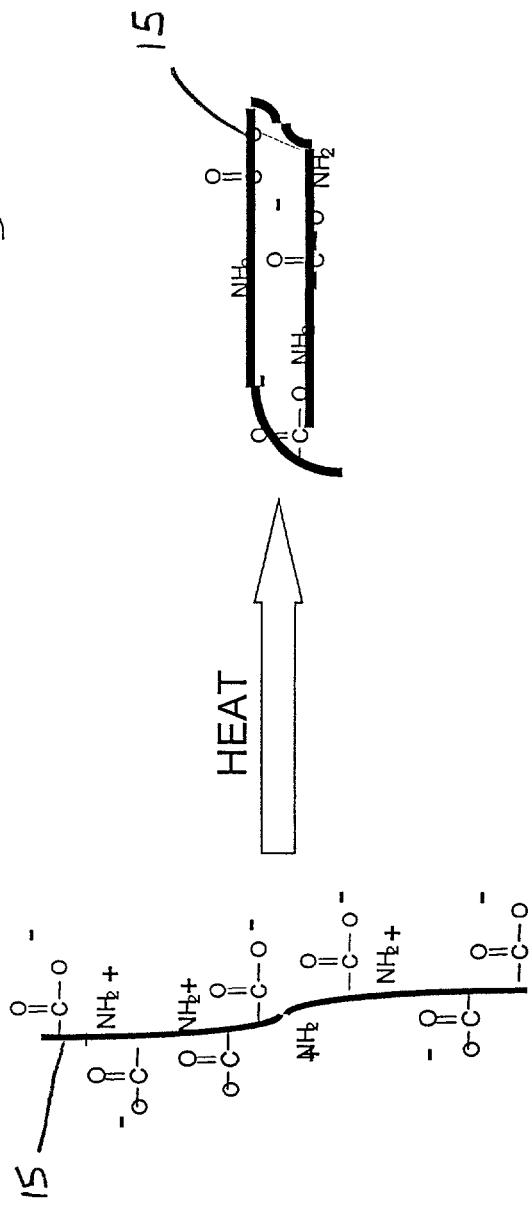
Figure 3:
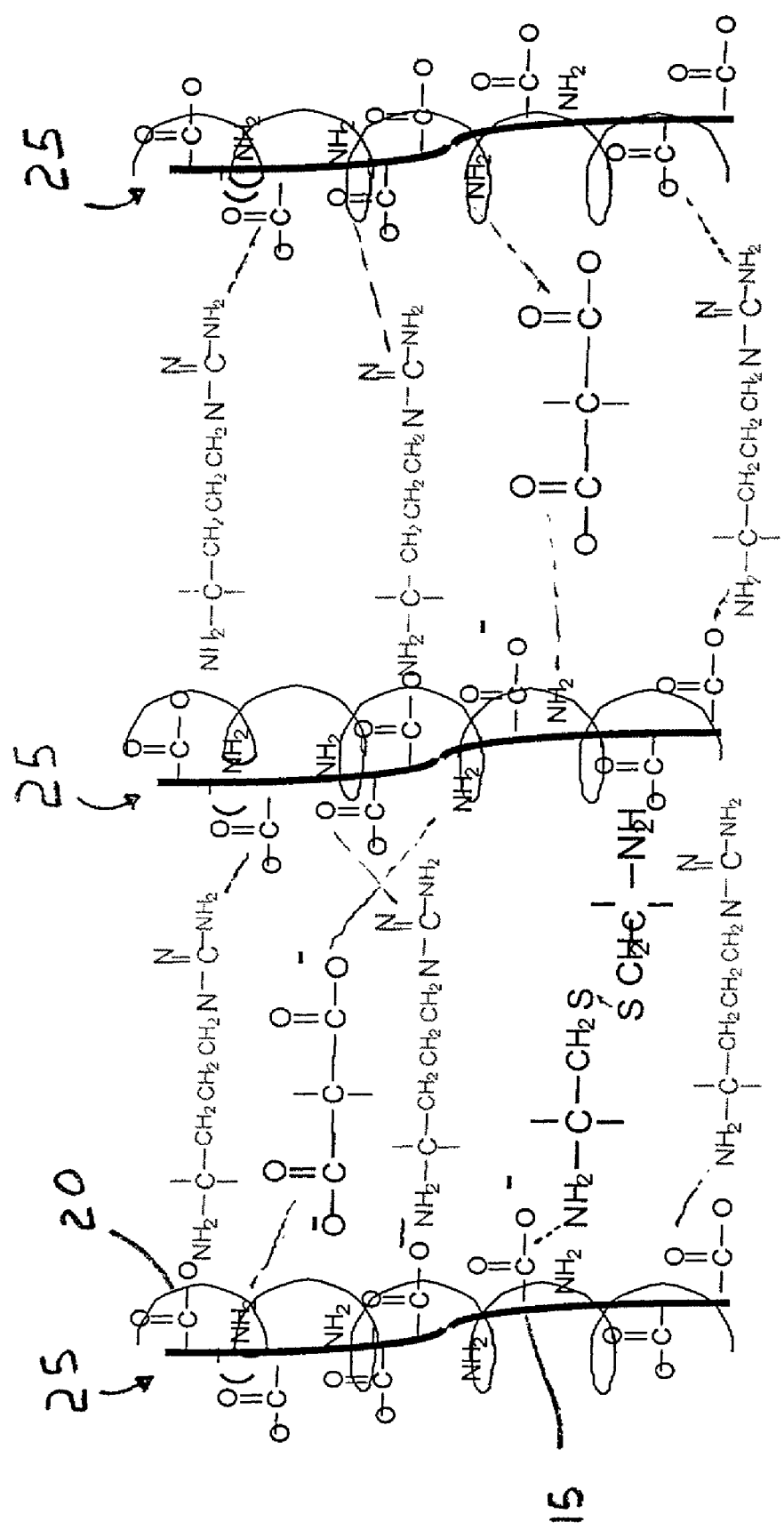

Having thus described the invention in general terms, reference will now be made to the accompanying drawings, wherein:

FIG. 1 illustrates formation of open alpha chains derived from collagen monomers;

FIGS. 2A and 2B illustrate the effect of the association of the alpha chains with dextran;

FIG. 3 illustrates the effect of other matrix additives; and

Figure 4:
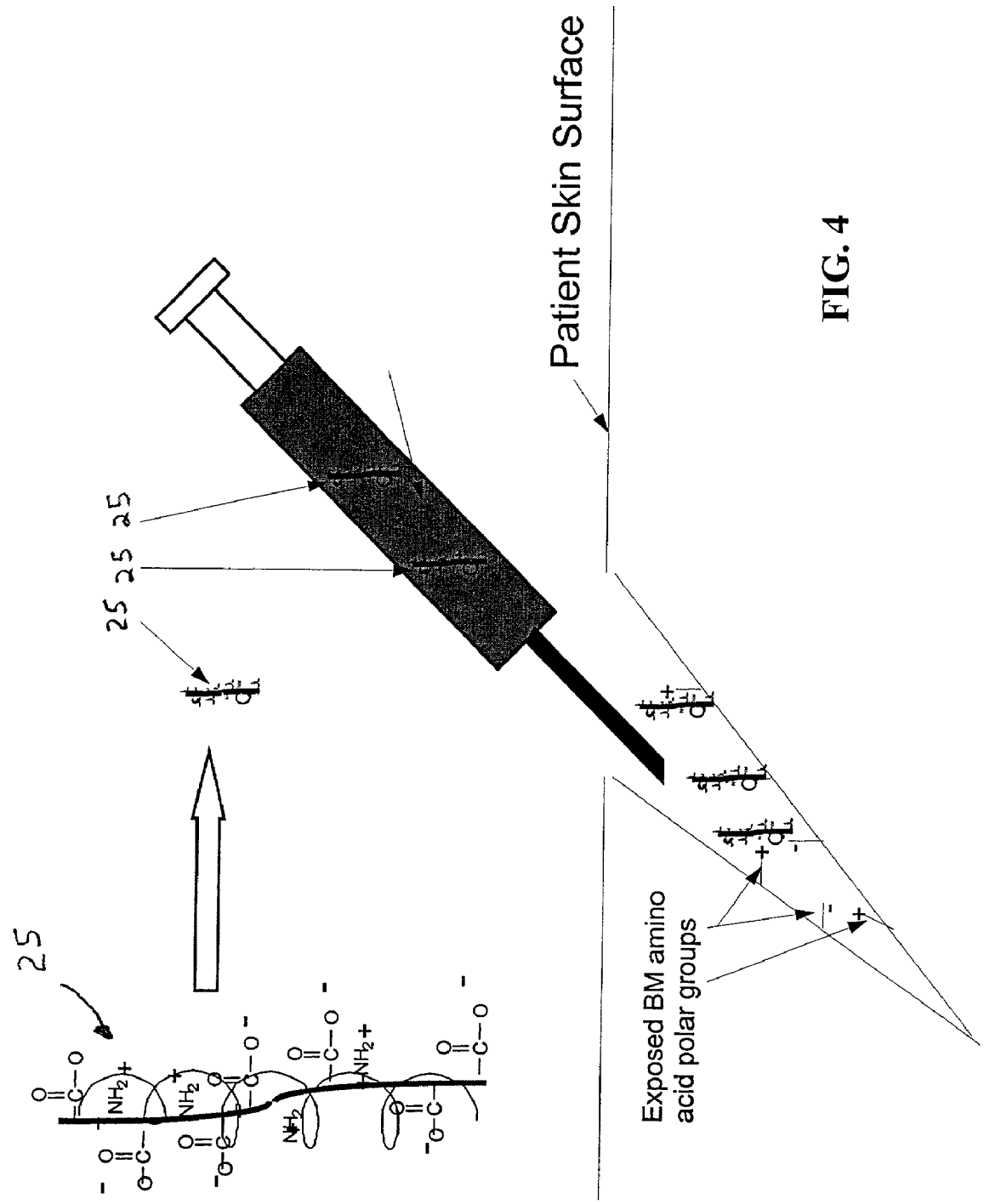

FIG. 4 illustrates binding of the matrix to the basement membrane (BM) of a patient.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Early in fetal development, a more open form of collagen (compared to tightly bound mature collagen) is associated with large carbohydrate molecules, and serves as the predominant tissue scaffolding. It is believed that attachment of differentiated or incompletely differentiated cells of mescenchymal origin to this polar, proteoglycan-like, collagen scaffolding results in a specific host tissue response. This response is to guide the differentiation of mesenchymal tissue into endothelial cells, subsequently organizing into blood vessels, and finally differentiating into primitive blood cells prior to the differentiation of bone marrow.

Although not bound by any particular theory, the present invention is intended to provide a matrix scaffolding designed to maximize the polar amino acid hydrogen bonding sites found in alpha chains derived from collagen. These alpha chains or gelatin are preferably derived from pig gelatin, and stabilized by 500,000 molecular weight dextran, or other long-chain carbohydrates, added while the alpha chains are heated. The positively charged polar groups of the collagen-derived alpha chains are then able to associate with the negatively charged —OH groups of the repeating glucose units found in the dextran. The gelatin and the dextran form a proteoglycan-type structure. FIGS. 1–4 illustrate the interaction between the various components of the preferred embodiment of the matrix of the invention and interaction between the matrix and the tissue of a patient.

FIG. 1 illustrates the creation of polar alpha chains 15 from tropocollagen 10 derived from mature collagen. Heating tropocollagen 10 disrupts the hydrogen bonds that tightly contain the triple stranded monomers in mature collagen. By breaking these hydrogen bonds, the polar amine and carboxylic acid groups are now available for binding to polar groups from other sources or themselves.

FIGS. 2A–2B illustrate stabilization of the matrix monomeric scaffolding by the introduction of a long-chain carbohydrate 20, such as dextran. As shown in FIG. 2B, without the long-chain carbohydrate 20, the alpha chain 15 will form hydrogen bonds between the amino and carboxylic acid groups within the linear portion of the monomer and fold upon itself, thus limiting available sites for cellular attachment. As depicted in FIG. 2A, the long-chain carbohydrate 20 serves to hold the alpha chain 15 open by interfering with this folding process.

FIG. 3 illustrates the effect of polar amino acids and/or L-cysteine added to stabilize the monomer/carbohydrate units 25 by linking the exposed monomer polar sites to, for example, arginine's amine groups or glutamic acid's carboxylic acid groups. Furthermore, disulfide linkages can be formed between L-cysteine molecules (thereby forming cystine), which in turn forms hydrogen bonds to the monomeric alpha chains 15. The hydrogen bonds formed between these additional amino acids and monomer/dextran units 25 are broken when the matrix is liquefied upon heating, and the polar groups are freed to attach the monomer/dextran units to exposed patient tissue surfaces upon injection. In preferred embodiments, EDTA or a salt thereof is also present to chelate divalent cations and thereby prevent divalent cations from being preferentially attracted to the exposed polar groups of the monomer/carbohydrate units 25 to the exclusion of the polar amino acids.

FIG. 4 shows attachment of the matrix to patient tissue by hydrogen bonding to exposed tissue amino acids. Exposure of these amino acids is easily achieved by tearing of the tissue with a hypodermic needle at the time of injection. The exposed polar groups of the basement membrane (BM) of the patient's tissue readily bind to the solid, scaffolding portion of the matrix enhanced by the polar amino acids. The aqueous portion is believed to be absorbed over a period of minutes to hours at normal body temperature.

Normally, the tearing of tissue secondary to injection trauma stimulates production and release of nitric oxide, initiating recruitment of immune and inflammatory cells that phagocytise or release chemicals to destroy foreign substances. By providing local and temporal inhibition of nitric oxide and superoxide release and production, nitric oxide inhibitors, such as aminoguanidine and cysteine, and superoxide inhibitors, such as EDTA, allow the collagen derived alpha chain/dextran units 25 to bind and become integrated on the exposed tissue surface. The alpha chain/dextran units 25 then serve as the scaffolding on which formerly differentiated host cells de-differentiate into "mesenchymoid" morphology. This de-differentiation process is followed by integration of these incompletely differentiated cells into host tissue. These mesenchymoid cells are then able to promote areas of their genome that leads to differentiation into fibroblasts, endothelial cells, and primitive blood forms. Hair follicles, which are dependent on healthy surrounding structures such as connective tissue and blood vessels, appear as part of the complete skin architecture in various portions of the body in humans and other animals. Some researchers have demonstrated a common embryologic origin for developing vascular endothelium (blood vessel lining) and hair follicles in mice (See Pennisi D., Bowles J., Nagy A., Muscat G., Koopman P., Mice null for sox 18 are viable and display a mild coat defect, *Mol. Cell. Biol.*, December 2000; 20(24):9331–6). In any case, hair follicles have a dermal and epidermal component, and result at least in part from mesenchymal tissues.

By providing a proteoglycan-like scaffolding similar to that found in the early stages of fetal development, and using structural stabilizers that serve a secondary purpose in enhancing host response to the scaffolding upon injection, the matrix serves as a biocompatible device capable of increasing vascularization and local tissue and hair follicle regeneration. Because the matrix promotes tissue regeneration, as occurs during embryogenesis and fetogenesis where similar types of scaffolding are present, it has now been discovered that the matrix of the invention can also be used to successfully stimulate hair growth in a patient, such as in and around a surgical wound or ulcer.

Components of the Matrix

The matrix comprises a gelatin component. Although denatured collagen is the preferred gelatin component, other gelatinous components characterized by a backbone comprised of long chain sequences of amino acids having polar groups whose intramolecular hydrogen bonds can be broken in order to expose the polar groups to interaction with other molecules can be used. For example, boiled agarose, alginate, keratin, aminoglycans, proteoglycans and the like could be used as the gelatin component. In one embodiment, the gelatin is porcine gelatin from partially hydrolyzed collagen derived from skin tissue.

The gelatin is present at a concentration of about 0.01 to about 40 mM, preferably about 0.05 to about 30 mM, most preferably about 1 to about 5 mM. Advantageously, the gelatin concentration is approximately 1.6 mM. The above concentrations provide a solid phase at storage temperature (below about 33° C.) and a liquid phase at treatment temperature (about 35 to about 40° C.). Intact collagen may be added in small amounts to provide an additional binding network. The final concentration of intact collagen is from about 0 to about 5 mM, preferably 0 to about 2 mM, most preferably about 0.05 to about 0.5 mM.

A long chain carbohydrate having a molecular weight of about 20,000 to about 1,000,000 Daltons is added to the gelatin component. Although dextran is a preferred carbohydrate, other high molecular weight carbohydrates may be used, such as amylopectin. The dextran loosely polymerizes around the gelatin component, thereby facilitating cell attachment by preventing folding of the gelatin scaffolding. The long chain carbohydrate is present at a concentration of about 0.01 to about 10 mM, preferably about 0.01 to about 1 mM, most preferably about 0.01 to about 0.1 mM. In one embodiment, dextran is present at a concentration of about 0.086 mM.

The gelatin/long chain carbohydrate component of the matrix of the present invention is mixed with a liquid composition. The liquid composition is preferably based upon a standard culture medium, such as Medium 199, supplemented with additives as described below.

The matrix preferably includes an effective amount of polar amino acids, such as arginine, lysine, histidine, glutamic acid, and aspartic acid, which further enhance the bioadhesiveness of the matrix. An effective amount is the amount necessary to increase the rigidity of the matrix and allow direct injection of the matrix into the patient. In one embodiment, the concentration of polar amino acids is about 3 to about 150 mM, preferably about 10 to about 65 mM, and more preferably about 15 to about 40 mM.

Advantageously, the added polar amino acids comprise L-glutamic acid, L-lysine, L-arginine, or mixtures thereof. The final concentration of L-glutamic acid is about 2 to about 60 mM, preferably about 5 to about 40 mM, most preferably about 10 to about 20 mM. In one embodiment, the concentration of L-glutamic acid is about 15 mM. The final concentration of L-lysine is about 0.5 to about 30 mM, preferably about 1 to about 15 mM, most preferably about 1 to about 10 mM. In one embodiment, the concentration of L-lysine is about 5 mM. The final concentration of L-arginine is about 1 to about 40 mM, preferably about 1 to about 30, most preferably about 5 to about 15 mM. In one embodiment, the final concentration of L-arginine is about 10 mM.

Additionally, the matrix preferably contains one or more nitric oxide inhibitors. Nitric oxide inhibitor is defined as any composition or agent that inhibits the production of nitric oxide or scavenges or removes existing nitric oxide. Nitric oxide, a pleiotropic mediator of inflammation, is a soluble gas produced by endothelial cells, macrophages, and specific neurons in the brain, and is active in inducing an inflammatory response. Nitric oxide and its metabolites are known to cause cellular death from nuclear destruction and related injuries. Preferred nitric oxide inhibitors include L-cysteine, L-arginine analogues (such as aminoguanidine, N-monomethyl-L-arginine, N-nitro-L-arginine, D-arginine and the like), cystine, heparin, and mixtures thereof.

In one embodiment, the matrix contains L-cysteine. L-cysteine acts as a nitric oxide scavenger and provides disulfide linkages, which increase the matrix's rigidity and resistance to force. The final concentration of L-cysteine is about 5 to about 500 $\mu$M, preferably about 10 to about 100 $\mu$M, most preferably about 15 to about 25 $\mu$M. In one embodiment, the final concentration is about 20 $\mu$M.

Advantageously, aminoguanidine is also added to the matrix of the present invention. As indicated above, aminoguanidine is an L-arginine analogue and acts as a nitric oxide inhibitor. The final concentration of aminoguanidine is about 5 to about 500 M, preferably about 10 to about 100 $\mu$M, most preferably about 15 to about 25 $\mu$M. In one embodiment, the final concentration is about 20 $\mu$M.

Additionally, the matrix of the present invention may include a superoxide inhibitor. A preferred superoxide inhibitor is ethylenediaminetetraacetic acid (EDTA) or a salt thereof. Superoxide is a highly toxic reactive oxygen species, whose formation is catalyzed by divalent transition metals, such as iron, manganese, cobalt, and sometimes calcium. Highly reactive oxygen species such as superoxide ($O_{2-}$) can be further converted to the highly toxic hydroxyl radical ($OH^-$) in the presence of iron. By chelating these metal catalysts, EDTA serves as an antioxidant. EDTA is also a divalent cation chelator, which increases the rigidity of the matrix by removing inhibition of $—NH_2$ to $—COOH$ hydrogen bonding. The concentration range for the superoxide inhibitor is about 0.01 to about 10 mM, preferably 1 to about 8 mM, most preferably about 2 to about 6 mM. In a preferred embodiment, the superoxide inhibitor is present at a concentration of about 4 mM.

Table 1 below lists particularly preferred key components of the matrix of the present invention along with suitable concentrations as well as preferred concentrations for each component.

TABLE 1

| Component | Concentration Range | Preferred Concentration |
|---|---|---|
| L-glutamic acid | 2 to 60 mM | 15 mM |
| L-lysine | .5 to 30 mM | 5.0 mM |
| Arginine | 1 to 40 mM | 10 mM |
| Gelatin | 0.01 to 40 mM | 1.6 mM |
| L-cysteine | 5 to 500 $\mu$M | 20 $\mu$M |
| Aminoguanidine | 5 to 500 $\mu$M | 20 $\mu$M |
| Intact collagen | 0 to 5 mM | 0 mM |
| EDTA | 0.01 to 10 mM | 4 mM |
| Dextran | 0.01 to 10 mM | 0.086 mM |

Matrix Preparation

Place 835 ml of Medium 199 into a stirred beaker. While stirring, heat the solution to 50° C. Pipette 63.28 $\mu$l of cysteine, 1 ml of L-glutamine and 200 $\mu$l of aminoguanidine into the stirred beaker. Add the following gamma-irradiated dry raw materials: 120 grams of denatured collagen, 50 grams of dextran, and 0.1 grams of intact collagen. Use a glass stirring rod to aid mixing of the dry materials into solution. Pipette 8 ml of EDTA into the solution. Pipette 5 ml of L-glutamic acid, 5 ml of L-lysine acetate, and 5 ml of arginine HCl into the stirred beaker. Note that the solution will turn yellow. Use 10% NaOH to adjust the pH of the matrix solution to a final pH of 7.40±0.1. Osmolality is preferably adjusted with sodium chloride and/or sterile water as need to a final osmolality of about 200 to about 400 mOsm.

Treatment Method

Preferably, a therapeutic amount of the matrix of the invention is administered intradermally or subdermally to a patient at a site where hair growth is desired. The treatment site can be the site of previous hair loss caused by, for example, pattern baldness, surgery or trauma. The patient can be any animal, including mammals such as dogs, cats and humans. The term "therapeutic amount" refers to the amount required to stimulate "normal" hair growth at the treatment site, meaning the hair growth experienced at the site prior to the pattern baldness, surgery, etc. In the case of pattern baldness, the therapeutic amount is the amount needed to stimulate normal full-thickness pigmented hair growth as opposed to the unpigmented vellus hair normally associated with the condition. The therapeutic amount will be primarily determined by the size of the treatment area. As an example, an injection in the scalp surface would preferably comprise about 0.1 to about 5 ml of matrix per 2.5 cm of "injection track", depending on the gauge of the needle. A large diameter needle would enable a greater volume of matrix to be placed in the injection site than a smaller diameter needle. "Injection track" refers to the total linear distance that will be traversed during matrix administration. Preferably, the therapeutic amount is sufficient to provide a uniform scaffolding for cellular attachment and differentiation in the proximal location of hair follicles at the treatment site, which is within or just below the dermis skin layer.

The method of application of the matrix should result in contact between the matrix and exposed polar groups of the basement membrane of the patient's tissue. A preferred method of administering the matrix is by injection, wherein the needle itself provides the necessary tearing of tissue that exposes cellular attachment sites capable of integration with the injected matrix.

EXPERIMENTAL

Example 1

A diabetic vascular lesion on a spontaneously diabetic, hyperlipidemic dog was treated with a single injection of the matrix (having the approximate concentrations and ingredients listed in Table 1) around the perimeter and centrally within the lesion. The total volume of injected matrix was about 5–10 ml in each lesion. The lesion was located on the right rear elbow. Two days post-injection, hyperemia was evident in the lesion, but no swelling or inflammation.

The lesion was completely closed within 6 days, with new skin and hair growth over the site of the lesion. A biopsy of the site was taken seven months after treatment. Histologic views of the site showed intact epidermis, dermis, hair follicles, and vascularization in the area of treatment.

Example 2

In another study, two of three rabbits with partial thickness skin ulcers on the back secondary to surgical ligation of peripheral blood vessels received matrix injections circumferentially and centrally within the ulcer. After four days, the two treated lesions were greatly reduced in size and by day 21 were completely healed. Of particular note is the hair regeneration that occurred in the treated rabbits. The third rabbit with an ulcer that was not treated with the matrix demonstrated incomplete healing of the original lesion at 21 days, with appearance of a new ulcer, and no hair growth.

Many modifications and other embodiments of the invention will come to mind to one skilled in the art to which this invention pertains having the benefit of the teachings presented in the foregoing descriptions and associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of stimulating hair growth, comprising administering a therapeutic amount of a hydrogel matrix in liquid form to an intradermal or subdermal site where hair growth is desired, the matrix composition comprising gelatin and a long chain carbohydrate, wherein the hydrogel matrix is solid at temperatures below about 33° C.

2. The method of claim 1, wherein the matrix comprises about 0.01 to about 40 mM gelatin.

3. The method of claim 1, wherein the gelatin comprises denatured collagen.

4. The method of claim 1, wherein the long chain carbohydrate comprises dextran.

5. The method of claim 4, wherein the matrix comprises about 0.01 to about 10 mM dextran.

6. The method of claim 1, wherein the long chain carbohydrate has a molecular weight of about 20,000 to about 1,000,000 Daltons.

7. The method of claim 1, wherein the matrix further comprises an effective amount of polar amino acids selected from the group consisting of arginine, lysine, histidine, glutamic acid, and aspartic acid.

8. The method of claim 7, wherein the effective amount of polar amino acids comprises about 3 to about 150 mM of polar amino acids.

9. The method of claim 7, wherein the effective amount of polar amino acids comprises about 10 to about 65 mM of polar amino acids.

10. The method of claim 7, wherein the polar amino acids are selected from the group consisting of arginine, glutamic acid, lysine and mixtures thereof.

11. The method according to claim 10, wherein the matrix comprises:
about 2 to about 60 mM of L-glutamic acid;
about 0.5 to about 30 mM of L-lysine; and
about 1 to about 40 mM of arginine.

12. The method of claim 11, wherein the matrix comprises:
about 5 to about 40 mM of L-glutamic acid;
about 1 to about 15 mM of L-lysine; and
about 1 to about 30 mM of arginine.

13. The method according to claim 10, wherein the effective amount of polar amino acids comprises about 2 to about 60 mM of L-glutamic acid.

14. The method according to claim 10, wherein the effective amount of polar amino acids comprises about 1 to about 40 mM of arginine.

15. The method of claim 10, wherein the effective amount of polar amino acids comprises about 0.5 to about 30 mM of L-lysine.

16. The method of claim 1, wherein the matrix further comprises at least one nitric oxide inhibitor.

17. The method of claim 16, wherein the nitric oxide inhibitor is selected from the group consisting of L-cysteine, L-arginine analogues, cystine, heparin, and mixtures thereof.

18. The method of claim 16, wherein the nitric oxide inhibitor is present in an amount of about 5 to about 1000 $\mu$M.

19. The method of claim 16, wherein the nitric oxide inhibitor is present in an amount of about 20 to about 200 $\mu$M.

20. The method of claim 1, wherein the matrix further comprises about 5 to about 500 $\mu$M of L-cysteine.

21. The method of claim 20, wherein the matrix comprises about 15 to about 25 $\mu$M of L-cysteine.

22. The method of claim 1, wherein the matrix further comprises about 5 to about 500 $\mu$M of an L-arginine analogue.

23. The method of claim 22, wherein the L-arginine analogue comprises aminoguanidine.

24. The method of claim 22, wherein the matrix comprises about 15 to about 25 $\mu$M of an L-arginine analogue.

25. The method of claim 1, wherein the matrix further comprises a superoxide inhibitor.

26. The method of claim 25, wherein the superoxide inhibitor comprises ethylenediaminetetraacetic acid (EDTA) or a salt thereof.

27. The method of claim 25, wherein the superoxide inhibitor is present in an amount of about 1 to about 8 mM.

28. The method of claim 1, wherein the gelatin comprises denatured collagen and the long chain carbohydrate comprises dextran.

29. The method of claim 1, wherein said administering step comprises injecting the matrix into one or more intradermal or subdermal locations.

30. A method of stimulating hair growth, comprising administering a therapeutic amount of a hydrogel matrix in liquid form to an intradermal or subdermal site where hair growth is desired, the matrix composition comprising denatured collagen, dextran, and an effective amount of polar amino acids selected from the group consisting of arginine, lysine, histidine, glutamic acid, and aspartic acid, wherein the hydrogel matrix is solid at temperatures below about 33° C.

31. The method of claim 30, wherein the effective amount of polar amino acids comprises about 3 to about 150 mM of polar amino acids.

32. The method of claim 31, wherein the effective amount of polar amino acids comprises about 10 to about 65 mM of polar amino acids.

33. The method of claim 30, wherein the polar amino acids are selected from the group consisting of arginine, glutamic acid, lysine and mixtures thereof.

34. The method according to claim 33, wherein the matrix comprises:
about 2 to about 60 mM of L-glutamic acid;
about 0.5 to about 30 mM of L-lysine; and
about 1 to about 40 mM of arginine.

35. The method of claim 30, wherein the matrix further comprises at least one nitric oxide inhibitor.

36. The method of claim 35, wherein the nitric oxide inhibitor is selected from the group consisting of L-cysteine, L-arginine analogues, cystine, heparin, and mixtures thereof.

37. The method of claim 35, wherein the nitric oxide inhibitor is present in an amount of about 5 to about 1000 $\mu$M.

38. The method of claim 35, wherein the nitric oxide inhibitor is present in an amount of about 20 to about 200 $\mu$M.

39. The method of claim 30, wherein the matrix further comprises about 5 to about 500 $\mu$M of L-cysteine.

40. The method of claim 30, wherein the matrix further comprises about 5 to about 500 $\mu$M of an L-arginine analogue.

41. The method of claim 30, wherein the matrix further comprises a superoxide inhibitor.

42. The method of claim 41, wherein the superoxide inhibitor comprises ethylenediaminetetraacetic acid (EDTA) or a salt thereof.

43. The method of claim 30, wherein said administering step comprises injecting the matrix into one or more intradermal or subdermal locations.

* * * * *